US008226553B2

(12) United States Patent
Shelton, IV et al.

(10) Patent No.: US 8,226,553 B2
(45) Date of Patent: Jul. 24, 2012

(54) ACCESS DEVICE WITH INSERT

(75) Inventors: Frederick E. Shelton, IV, Hillsboro, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 211 days.

(21) Appl. No.: 12/712,269

(22) Filed: Feb. 25, 2010

(65) Prior Publication Data

US 2010/0249526 A1   Sep. 30, 2010

Related U.S. Application Data

(63) Continuation-in-part of application No. 12/479,418, filed on Jun. 5, 2009.

(60) Provisional application No. 61/165,080, filed on Mar. 31, 2009.

(51) Int. Cl.
*A61B 1/32* (2006.01)
(52) U.S. Cl. .................. 600/208; 600/206; 600/203
(58) Field of Classification Search .................. 600/207, 600/208, 31, 115, 116, 201, 206, 470, 204, 600/213, 215, 203; 604/26, 256; 602/63
See application file for complete search history.

(56) References Cited

U.S. PATENT DOCUMENTS

| | | | |
|---|---|---|---|
| 2,129,391 A | 9/1938 | Wappler | |
| 3,402,710 A | 9/1968 | Paleschuck | |
| 3,503,396 A | 3/1970 | Pierie et al. | |
| 3,654,965 A | 4/1972 | Gramain | |
| 4,041,931 A | 8/1977 | Elliott et al. | |
| 4,048,987 A | 9/1977 | Hurson | |
| 4,112,932 A | 9/1978 | Chiulli | |
| 4,120,302 A | 10/1978 | Ziegler | |
| 4,306,545 A | 12/1981 | Ivan et al. | |
| 4,373,532 A | 2/1983 | Hill et al. | |
| 4,402,683 A | 9/1983 | Kopman | |
| 4,417,888 A | 11/1983 | Cosentino et al. | |
| 4,559,947 A | 12/1985 | Renger et al. | |
| 4,669,473 A | 6/1987 | Richards et al. | |
| 4,821,719 A | 4/1989 | Fogarty | |
| 4,831,070 A | 5/1989 | McInally et al. | |
| 5,027,800 A | 7/1991 | Rowland | |
| 5,141,498 A | 8/1992 | Christian | |
| 5,183,471 A | 2/1993 | Wilk | |
| 5,197,955 A | 3/1993 | Stephens et al. | |
| 5,207,213 A | 5/1993 | Auhll et al. | |

(Continued)

FOREIGN PATENT DOCUMENTS

CA     2095064     11/1993

(Continued)

OTHER PUBLICATIONS

Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).

(Continued)

*Primary Examiner* — Pedro Philogene

(57) ABSTRACT

Various devices and methods are provided with respect to inserting multiple surgical instruments through a single surgical access device. A medical device including a flexible tissue retractor and a releasable insert having multiple instrument openings is disclosed. The insert can be in the form of an insert assembly including multiple components. A method of using the insert is also described.

20 Claims, 13 Drawing Sheets

U.S. PATENT DOCUMENTS

| | | |
|---|---|---|
| 5,209,737 A | 5/1993 | Ritchart et al. |
| 5,209,741 A | 5/1993 | Spaeth |
| 5,269,772 A | 12/1993 | Wilk |
| 5,308,336 A | 5/1994 | Hart et al. |
| 5,330,437 A | 7/1994 | Durman |
| 5,342,315 A | 8/1994 | Rowe et al. |
| 5,345,927 A | 9/1994 | Bonutti |
| 5,362,294 A | 11/1994 | Seitzinger |
| 5,366,478 A | 11/1994 | Brinkerhoff et al. |
| 5,368,597 A | 11/1994 | Pagedas |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,443,452 A | 8/1995 | Hart et al. |
| 5,443,484 A | 8/1995 | Kirsch et al. |
| 5,480,410 A | 1/1996 | Cuschieri et al. |
| 5,501,653 A | 3/1996 | Chin |
| 5,520,609 A | 5/1996 | Moll et al. |
| 5,545,123 A | 8/1996 | Ortiz et al. |
| 5,545,179 A | 8/1996 | Williamson, IV |
| 5,547,458 A | 8/1996 | Ortiz et al. |
| 5,569,205 A | 10/1996 | Hart et al. |
| 5,569,254 A | 10/1996 | Carison et al. |
| 5,582,577 A | 12/1996 | Lund et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,624,381 A | 4/1997 | Kieturakis |
| 5,630,831 A | 5/1997 | Lahr |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,851 A | 4/1998 | Moll et al. |
| 5,772,654 A | 6/1998 | Leyva |
| 5,782,812 A | 7/1998 | Hart et al. |
| 5,793,113 A | 8/1998 | Oda |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,840,078 A | 11/1998 | Yerys |
| 5,853,395 A | 12/1998 | Crook et al. |
| 5,865,807 A | 2/1999 | Blake, III |
| 5,876,447 A | 3/1999 | Arnett |
| 5,891,013 A | 4/1999 | Thompson |
| 5,893,878 A | 4/1999 | Pierce |
| 5,906,577 A * | 5/1999 | Beane et al. ................. 600/207 |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,736 A | 2/2000 | de la Torre et al. |
| 6,033,428 A | 3/2000 | Sardella |
| RE36,702 E | 5/2000 | Green et al. |
| 6,074,419 A | 6/2000 | Healy et al. |
| 6,077,288 A | 6/2000 | Shimomura et al. |
| 6,086,603 A | 7/2000 | Termin et al. |
| 6,093,141 A | 7/2000 | Mosseri et al. |
| 6,110,154 A | 8/2000 | Shimorura et al. |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,156,184 A | 12/2000 | Antonucci et al. |
| 6,159,200 A | 12/2000 | Verdura et al. |
| 6,162,196 A | 12/2000 | Hart et al. |
| 6,165,184 A | 12/2000 | Verdura et al. |
| 6,171,282 B1 | 1/2001 | Ragsdale |
| 6,197,034 B1 | 3/2001 | Gvozdic et al. |
| 6,217,555 B1 | 4/2001 | Hart et al. |
| 6,220,248 B1 | 4/2001 | Voegele et al. |
| 6,228,055 B1 | 5/2001 | Foester et al. |
| 6,245,052 B1 | 6/2001 | Orth et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,262,196 B1 | 7/2001 | Mecking |
| 6,264,599 B1 | 7/2001 | Slater et al. |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,347,490 B1 | 2/2002 | Spengler |
| 6,348,034 B1 | 2/2002 | Thompson |
| 6,352,503 B1 | 3/2002 | Matsui et al. |
| 6,425,903 B1 | 7/2002 | Voegele |
| 6,447,443 B1 | 9/2002 | Koegh et al. |
| 6,447,489 B1 | 9/2002 | Peterson |
| 6,454,783 B1 | 9/2002 | Piskun |
| 6,458,077 B1 | 10/2002 | Bogbel et al. |
| 6,471,714 B1 | 10/2002 | Kim |
| 6,485,467 B1 | 11/2002 | Crook et al. |
| 6,551,270 B1 | 4/2003 | Bimbo et al. |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,623,426 B2 | 9/2003 | Bonadio et al. |
| 6,634,883 B2 | 10/2003 | Ranalli |
| 6,669,674 B1 | 12/2003 | Wacoviak et al. |
| 6,702,787 B2 | 3/2004 | Recenet et al. |
| 6,706,033 B1 | 3/2004 | Martinez et al. |
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyas et al. |
| 6,810,880 B1 | 11/2004 | Jennings, Jr. et al. |
| 6,821,247 B2 | 11/2004 | Vierra et al. |
| 6,846,287 B2 | 1/2005 | Bonadio et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 6,994,712 B1 | 2/2006 | Fisher et al. |
| 7,008,377 B2 | 3/2006 | Beane et al. |
| 7,014,628 B2 | 3/2006 | Bousquet |
| 7,047,063 B2 | 5/2006 | Burbank et al. |
| 7,052,454 B2 | 5/2006 | Taylor |
| 7,083,576 B2 | 8/2006 | Zarins et al. |
| 7,083,626 B2 * | 8/2006 | Hart et al. ................. 606/108 |
| 7,118,528 B1 | 10/2006 | Piskun |
| 7,163,510 B2 | 1/2007 | Kahle et al. |
| 7,214,185 B1 | 5/2007 | Rosney et al. |
| 7,311,660 B2 | 12/2007 | Gomez |
| 7,338,473 B2 | 3/2008 | Cmapbell et al. |
| 7,344,547 B2 | 3/2008 | Piskun |
| 7,393,322 B2 | 7/2008 | Wenchell |
| 7,416,533 B2 | 8/2008 | Gellman et al. |
| 7,438,702 B2 | 10/2008 | Hart et al. |
| 7,585,288 B2 | 9/2009 | Haberland et al. |
| 7,967,791 B2 * | 6/2011 | Franer et al. ............. 604/167.06 |
| 2001/0034528 A1 | 10/2001 | Foester et al. |

| | | |
|---|---|---|
| 2001/0053510 A1 | 12/2001 | Ranalli |
| 2002/0007112 A1 | 1/2002 | Rupp et al. |
| 2002/0026201 A1 | 2/2002 | Foester et al. |
| 2002/0038179 A1 | 3/2002 | Tschrroster et al. |
| 2002/0103434 A1 | 8/2002 | Swanson |
| 2002/0156432 A1 | 10/2002 | Racenet et al. |
| 2002/0193815 A1 | 12/2002 | Foester et al. |
| 2003/0028179 A1 | 2/2003 | Piskun |
| 2003/0113540 A1 | 6/2003 | Anderson et al. |
| 2003/0139756 A1 | 7/2003 | Brustad |
| 2003/0206860 A1 | 11/2003 | Bleyer et al. |
| 2003/0225420 A1 | 12/2003 | Wardle |
| 2004/0015185 A1 | 1/2004 | Ewers et al. |
| 2004/0023161 A1 | 2/2004 | Yamaguchi et al. |
| 2004/0024304 A1 | 2/2004 | Foester et al. |
| 2004/0106942 A1 | 6/2004 | Taylor et al. |
| 2004/0106986 A1 | 6/2004 | Anderson et al. |
| 2004/0138528 A1 | 7/2004 | Richter et al. |
| 2004/0147933 A1 | 7/2004 | McGovern |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Herron |
| 2005/0222582 A1 | 10/2005 | Wenchell |
| 2005/0229501 A1 | 10/2005 | Grossman et al. |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0020241 A1 | 1/2006 | Piskun et al. |
| 2006/0020281 A1 | 1/2006 | Smith |
| 2006/0071432 A1 | 4/2006 | Staudner |
| 2006/0149137 A1 | 7/2006 | Pinglrton et al. |
| 2006/0161050 A1* | 7/2006 | Butler et al. ............ 600/208 |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburg, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0118021 A1 | 5/2007 | Pokorney |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0119821 A1 | 5/2008 | Agnuihotri et al. |
| 2008/0183044 A1 | 7/2008 | Colleran et al. |
| 2008/0255519 A1 | 10/2008 | Piskun et al. |
| 2009/0005799 A1 | 1/2009 | Franer et al. |
| 2009/0012477 A1 | 1/2009 | Norton et al. |
| 2009/0036738 A1 | 2/2009 | Cuschieri et al. |
| 2009/0062618 A1 | 3/2009 | Drew et al. |

FOREIGN PATENT DOCUMENTS

| | | |
|---|---|---|
| EP | 0568383 | 1/1993 |
| EP | 0646358 | 4/1995 |
| EP | 0776231 | 6/1997 |
| EP | 0996925 | 5/2000 |
| EP | 1219251 | 7/2002 |
| EP | 1219252 | 7/2002 |
| EP | 1219253 | 7/2002 |
| EP | 1350476 | 10/2004 |
| EP | 1731105 | 12/2006 |
| FR | 2710270 | 3/1995 |
| JP | 2000033089 | 2/2000 |
| JP | 2006320750 | 11/2006 |
| WO | WO 9608208 | 3/1996 |
| WO | WO 9729709 | 8/1997 |
| WO | WO 9735521 | 10/1997 |
| WO | WO 9810712 | 3/1998 |
| WO | WO 9903536 | 1/1999 |
| WO | WO 0030592 | 6/2000 |
| WO | WO 0032253 | 6/2000 |
| WO | WO 0239918 | 5/2002 |
| WO | WO 02058543 | 8/2002 |
| WO | WO 02094133 | 11/2002 |
| WO | WO 03/005890 | 1/2003 |
| WO | WO 03077730 | 9/2003 |
| WO | WO 2005087112 | 9/2005 |
| WO | WO 2005094432 | 10/2005 |
| WO | WO 2006110733 | 10/2006 |
| WO | WO 2007119232 | 10/2007 |
| WO | WO 2008012787 | 1/2008 |
| WO | WO 2008024502 | 2/2008 |

OTHER PUBLICATIONS

*Twentieth Edition—Illustrations of Surgical Instruments*, by the Kny-Scheerer Company, New York, USA, pp. 1003, 1026, 1028-1029, 1133, 2034, 2068-2069, 2097-2099, 2132, 2137, 2144, 2155-2156,. 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).

Webpage of Novare Surgical, Inc. featuring clamps (date of first publication unknown; downloaded Feb. 23, 2004; 1 page).

U.S. Appl. No. 12/242,333, filed Sep. 30, 2008.
U.S. Appl. No. 12/242,353, filed Sep. 30, 2008.
U.S. Appl. No. 12/242,381, filed Sep. 30, 2008.
U.S. Appl. No. 12/242,711, filed Sep. 30, 2008.
U.S. Appl. No. 12/242,721, filed Sep. 30, 2008.
U.S. Appl. No. 12/242,726, filed Sep. 30, 2008.
U.S. Appl. No. 12/242,765, filed Sep. 30, 2008.
U.S. Appl. No. 12/399,482, filed Mar. 6, 2009.
U.S. Appl. No. 12/399,625, filed Mar. 6, 2009.

* cited by examiner

ACCESS DEVICE WITH INSERT

This patent application incorporates by reference and claims priority to as a continuation in part of Devices and Methods for Providing Access Into a Body Cavity, U.S. Ser. No. 12/479,418, filed Jun. 5, 2009; and this patent application also incorporates by reference and claims priority to Provisional Patent Application Ser. No. 61/165,080 filed Mar. 31, 2009.

CROSS REFERENCE

The present application cross references and incorporates by reference the following commonly assigned US patent applications: U.S. Ser. No. 11/398,985 filed Apr. 5, 2006 and published as US20060247673; U.S. Ser. No. 11/399,181 filed Apr. 5, 2006; U.S. Ser. No. 11/399,145 filed Apr. 5, 2006; U.S. Ser. No. 11/399,149 filed Apr. 5, 2006; U.S. Ser. No. 11/399,044 filed Apr. 5, 2006; U.S. Ser. No. 11/399,172 filed Apr. 5, 2006; U.S. Ser. No. 11/399,045 filed Apr. 5, 2006; U.S. Ser. No. 12/242,765 filed Sep. 30, 2008; U.S. Ser. No. 12/242,711 filed Sep. 30, 2008; U.S. Ser. No. 12/242,721 filed Sep. 30, 2008; U.S. Ser. No. 12/242,383 filed Sep. 30, 3008; U.S. Ser. No. 12/242,333 filed Sep. 30, 2008; U.S. Ser. No. 12/242,353 filed Sep. 30, 2008; U.S. Ser. No. 12/242,381 filed Sep. 30, 2008; U.S. Ser. No. 12/399,625 filed Mar. 6, 2009; U.S. Ser. No. 12/399,633 filed Mar. 6, 2009; U.S. Ser. No. 12/399,547 filed Mar. 6, 2009; U.S. Ser. No. 12/399,656 filed Mar. 6, 2009; U.S. Ser. No. 12/399,482 filed Mar. 6, 2009; U.S. Ser. No. 12/399,473; U.S. Ser. No. 12/110,724 filed Apr. 28, 2008; U.S. Ser. No. 12/109,881 filed Apr. 25, 2008; U.S. Ser. No. 12/425 filed Apr. 29, 2008; and U.S. Ser. No. 12/172,349 filed Jul. 14, 2008.

FIELD OF THE INVENTION

The present invention relates to access devices, such as for providing surgical access into a body cavity.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s).

Recently, so-called "mini-laparoscopy" has been introduced utilizing 2-3 mm diameter straight trocar sleeves and laparoscopic instruments. When successful, mini-laparoscopy allows further reduction of abdominal wall trauma and improved cosmesis. Instruments used for mini-laparoscopic procedures are, however, generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller 2-3 mm incisions may still cause undesirable cosmetic outcomes and wound complications (bleeding, infection, pain, keloid formation, etc.).

Since the benefits of smaller and fewer body cavity incisions are proven, it would be desirable to perform an operation utilizing only a single incision in the navel. An umbilicus is well-hidden and the thinnest and least vascularized area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus or a surgical port located elsewhere while at the same time reducing or eliminating the "chopstick effect."

SUMMARY OF THE INVENTION

The present invention generally provides devices for allowing surgical access to an interior of a patient's body.

In one embodiment, the medical device comprises a tissue retractor and an insert releasably supported within a passageway associated with the tissue refractor. The insert may have an outer surface sized and shaped to deform a flexible member of the tissue retractor to provide at least a portion of the passageway with a predetermined size and shape.

The insert can be in the form of an insert assembly having a generally cylindrical outer surface sized to radially stretch a portion of the tissue retractor to have a generally circular or other suitable cross-section of predetermined diameter or width upon insertion of the insert within the passageway.

The tissue retractor may be a flexible tissue retractor which includes a flexible member, such as a flexible membrane, having a first end and a second end, and the insert may be releasably supported or otherwise releasably insertable within the passageway of the flexible tissue retractor.

In one embodiment, the insert comprises an assembly having an inner portion and an outer portion. The outer portion can have a generally cylindrical outer surface adapted to engage the inner surface of the passageway of the tissue retractor, and the inner portion may include a plurality of instrument openings aligned with instrument passageways rotatable with respect to the outer portion of the insert and the flexible tissue retractor.

The insert may comprise an assembly which includes an outer body portion sized and shaped to engage and deform a portion of the inner surface of a flexible tissue retractor, a housing disposed at least partially within the outer sleeve, at least one instrument opening in an upper surface of the housing, and at least one seal operatively associated with each instrument opening. The insert assembly may also include an instrument channel member in the form of a unitary, flexible structure defining a plurality of tubular instrument channels. Each tubular instrument channel may be independently deformable with respect to the housing and the other tubular instrument channels. The instrument channels and instrument openings may be rotatably supported with respect to the outer sleeve and the tissue retractor, such as by a bearing member In one embodiment the flexible tissue retractor comprises first and second deformable rings, and the insert is sized and shaped to pass through at least one of the rings without deforming the ring. The insert may be sized and shaped to deform a portion of a flexible member extending intermediate the first and second rings In one embodiment, an assembly comprising a flexible tissue retractor, an insert, and a sleeve is provided. The sleeve may be positioned in the flexible tissue retractor, and the insert may be pressed into the sleeve. The sleeve and insert may be removed together from the retractor without removing the retractor from the incision. The sleeve may be provided to assist in inserting and removing the insert, and the sleeve may be formed of a material having a relatively low coefficient of friction, and a relatively high puncture resistance and/or high toughness In one embodiment, a method for accessing a body cavity through in incision is provided. The method includes the steps of positioning a tissue retractor in the incision; and releasably positioning an insert having multiple instrument openings into the tissue retractor. The step of positioning the insert may be by pressing the insert into the tissue retractor, and may include deforming and/or stretching at least a portion of the tissue retractor. The method may include forming an incision, positioning a tissue retractor in the incision, positioning a sleeve to extend at least partially within the tissue retractor, and positioning an insert having one or more instrument openings into the sleeve In one embodiment, a medical device is provided including a tissue retractor, at least one insert having at least one instrument opening, where the insert is positionable, such as by pressing, at different insertion depths within a passageway of the tissue retractor.

In one embodiment, a method for accessing a body cavity includes the steps of positioning a flexible tissue retractor in the incision, wherein the tissue retractor provides a passageway extending through the incision; releasably positioning a first insert having at least one instrument opening in the passageway provided by the flexible tissue retractor; removing the first insert from the passageway provided by the tissue retractor; and positioning a second insert having at least one instrument opening in the passageway. The second insert can have a different number of instrument openings and/or a different size and/or a different shape than that of the first insert. The method can also include repositioning an insert to a second depth in the passageway of the retractor.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides a medical device, such as a surgical access assembly, that allows one or more surgical instruments to be inserted through a single incision surgical access device, such as at various depths of insertion, thereby allowing for ease of manipulation of instruments within a patient's body while maintaining insufflation.

Figure 1:
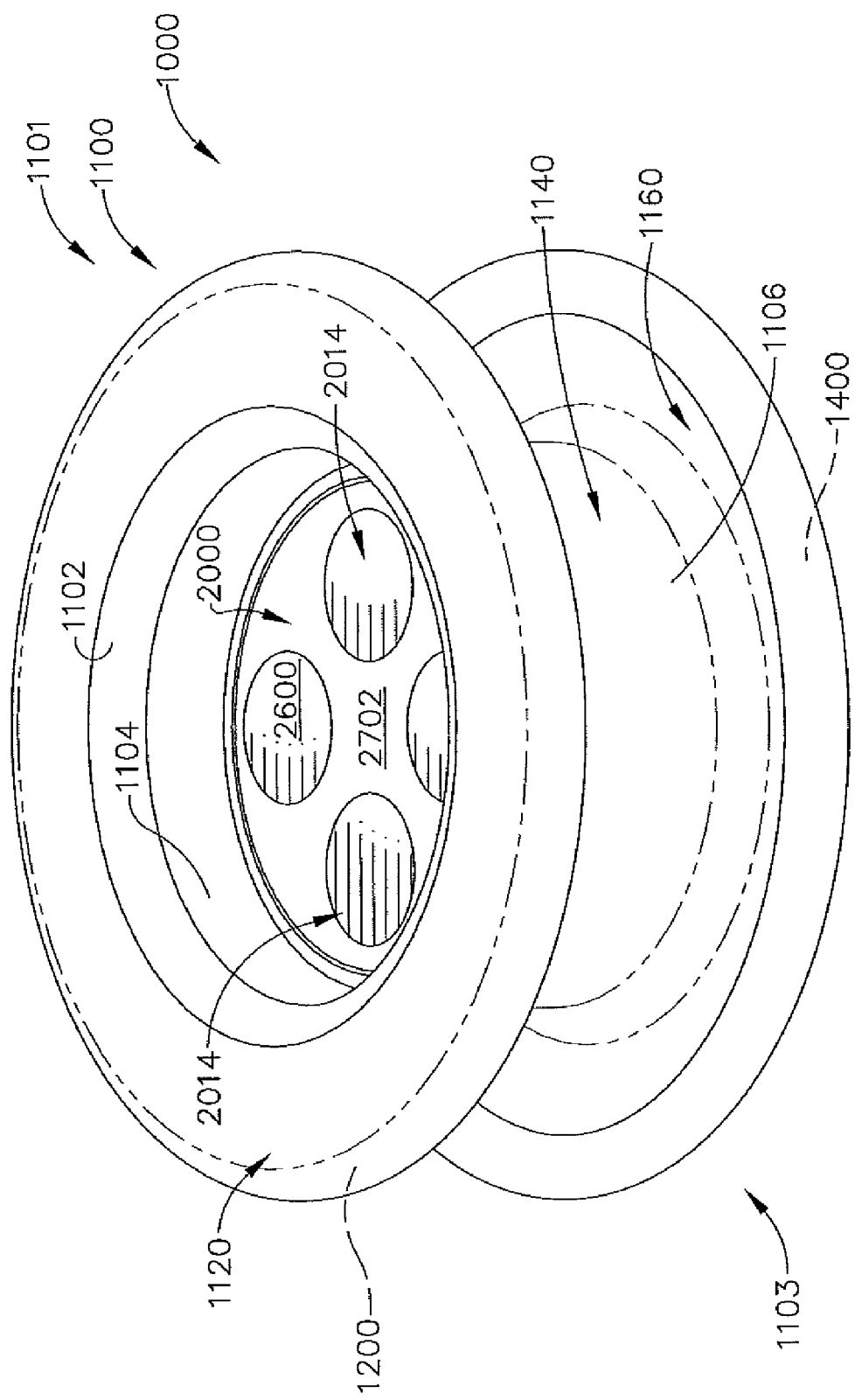
FIG. 1 is a perspective, proximal view showing an access device comprising an insert having at least one instrument opening releasably supported within a flexible tissue retractor, with the proximal end of the insert shown inserted to be positioned below an upper, proximal end of the flexible tissue retractor.
Figure 2:
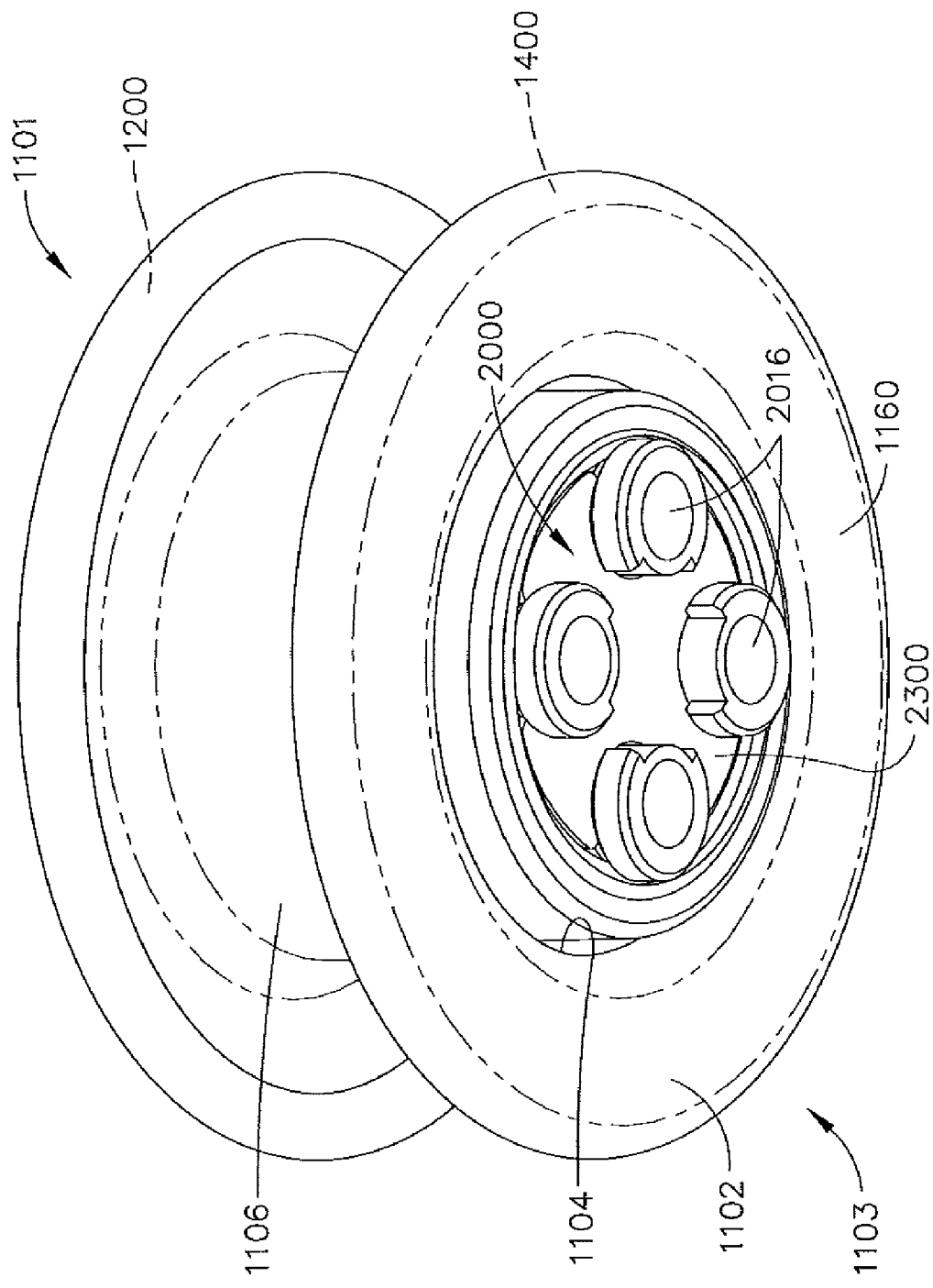
FIG. 2 is a perspective, distal view of the insert and flexible tissue retractor shown in FIG. 1, with a distal, bottom end of the insert shown visible from a lower, distal opening of the flexible tissue retractor.

FIG. 1 is a perspective view of the top, or proximal portion of the access assembly, and FIG. 2 is a perspective view of the bottom, or distal portion of the access assembly. Referring to FIGS. 1 and 2, in one embodiment the medical device is in the form of an access assembly comprising a flexible tissue refractor 1000 and an insert 2000 having at least one instrument opening 2014 (four instrument openings 2014 shown in FIG. 1, and four instrument exits 2016 shown in FIG. 2). The instrument openings 2014 may extend through a top surface 2702 of a portion of the insert, and the openings 2014 may be closed or otherwise obstructed by a membrane seal 2600, as described in more detail below.

The insert 2000 is shown releasably supported within a passageway 1104 defined by a flexible member 1100 of the retractor 1000. The phrase "releasably supported" in this context means the insert can be inserted and removed from the tissue refractor multiple times, including during a surgical procedure, without damaging or otherwise impairing the function of the refractor or the insert. In one illustrative example, the insert 2000 is releasably inserted by pressing (such as with a thumb or finger) the insert into the passageway of the retractor.

The flexible member 1100 can include a first generally annular shaped, outer or top portion 1120 (oriented generally horizontally in FIG. 1), a second generally annular shaped, inner portion 1160 (oriented generally horizontally and generally parallel to portion 1120 in FIG. 1), and a generally cylindrically shaped portion 1140 extending axially in a distal direction from portion 1120 to portion 1160.

The outer portion 1120 can be associated with a first, proximal end 1101 of the flexible member 1100, and the inner portion 1160 can be associated with a second, distal end 1103 of the flexible member 110. The outer portion 1120 is disposed outside the patient's body when the flexible retractor is positioned during surgery, and the inner portion 1160 is disposed within the patient, such as within a body cavity, during a surgical procedure. An inner surface of the generally cylindrical portion 1140 may provide most or substantially all of the passageway 1104, while an outer surface of the generally cylindrical portion 1140 may contact the walls of an incision when the flexible retractor 1000 is positioned during surgery, such as is shown in FIG. 3.

The flexible member 1100 may comprise a unitary, flexible membrane forming the portions 1120, 1140, and 1160, and having a first surface 1102 and a second surface 1106. The passageway 1104 of tissue retractor 1000 may be defined at least in part by a portion of the first surface 1102 facing radially inwardly in generally cylindrical portion 1140. The portion of the second surface 1106 associated with the generally cylindrical portion 1140 may face radially outwardly so as to contact or otherwise engage the tissue at the incision site.

The flexible tissue retractor 1000 may also comprise proximal and distal members for providing engagement of outer and inner portions of the retractor with outer and inner portions of the patient. For instance, the tissue retractor 1000 may include a resilient, outer (proximal) deformable ring 1200 and a resilient, inner (distal) deformable ring 1400. Rings 1200 and 1400 are shown in phantom in FIGS. 1 and 2, and in cross-section in FIG. 3. The flexible member 1100 is shown extending intermediate the rings 1200 and 1400, such that member 1100 extends from ring 1200 to ring 1400.

Figure 3:
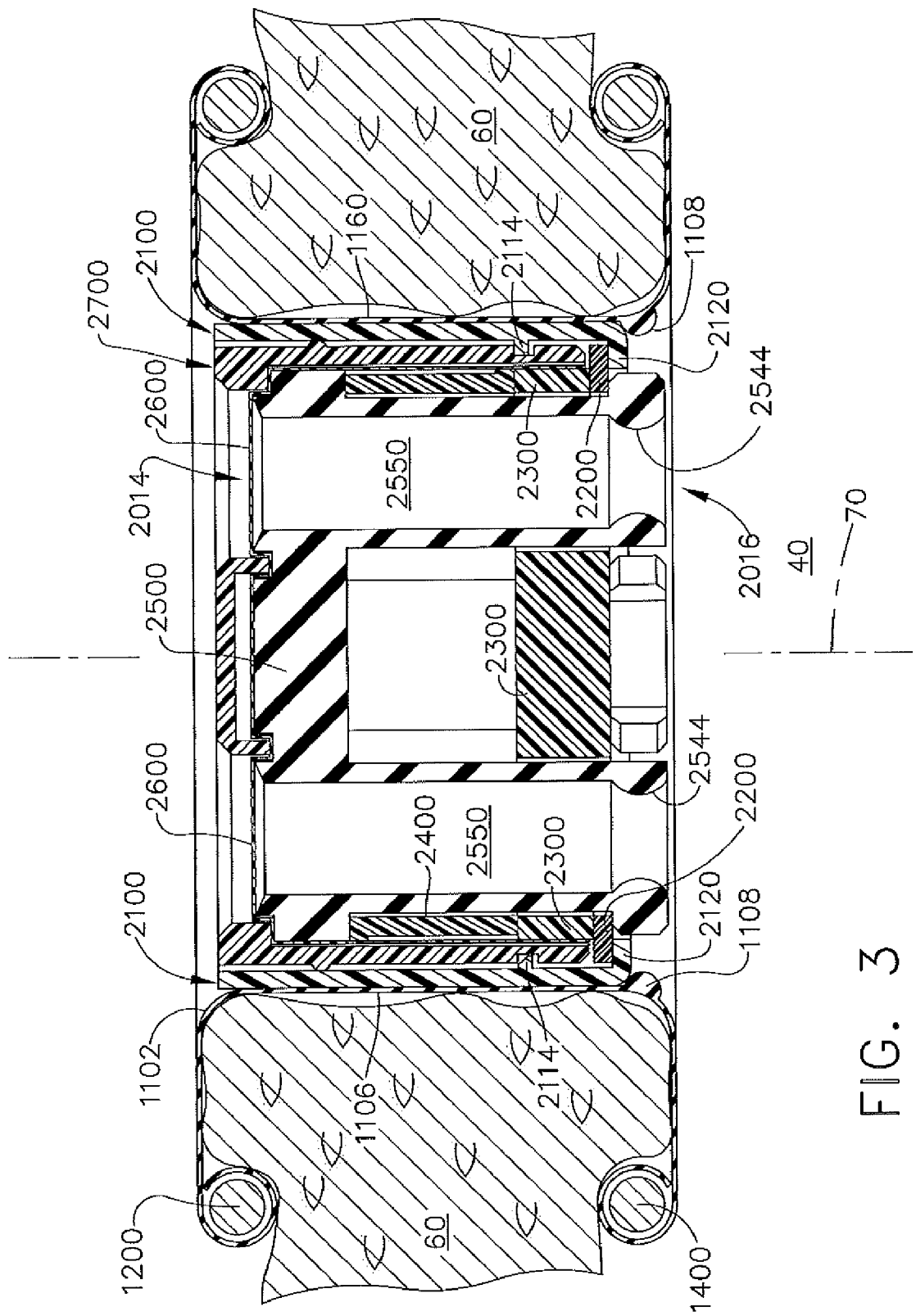
FIG. 3 is a cross-sectional view of a device of the type shown in FIG. 1.

FIG. 3 shows the access assembly of flexible refractor 1000 and insert 2000 positioned in an incision such that the distal portion 1160 of the retractor 1000 and the ring 1400 are disposed in the abdominal cavity 40, and the such that tissue 60 (including a portion of the abdominal wall) engages the surface 1106 of the flexible retractor.

The rings 1200 and 1400 can have any suitable closed or substantially closed configuration, including without limitation circular, oval, and elliptical configurations. By "resilient deformable ring" it is meant that the ring may be relatively easily deformed, such as by pressing opposite sides of the ring together with the fingers (and without any additional tools or aids), so that the ring may be inserted through a narrow incision in a body wall (e.g. the abdominal wall). For instance, the inner ring 1400 may be deformed, such as by pressing opposite sides of the ring together with the fingers, and inserted through an incision in the patient, such as an incision through the abdominal wall. Once the ring is fully inserted, the inner ring 1400 is able to resiliently return to its undeformed shape. The ring assists in securing the retractor 1000 within the incision by engaging the inside surface of the abdominal wall of the abdominal cavity.

The flexible member can comprise a flexible membrane of a resiliently deformable material, such as natural rubber, silicone, or a suitable deformable elastomer or elastomeric material. The deformable rings can be attached to the flexible membrane, or enclosed within rolled ends of the membrane. One suitable flexible tissue retractor comprising a flexible member with inner and outer deformable rings is a tissue retractor available from Hakko as Hakko FF0707.

The flexible tissue retractor can be provided in one or more sizes, and in one example has a length, or height (measured in the direction of axis 70 in FIG. 3) of between about 15 mm and about 30 mm, a maximum diameter corresponding to the diameter of the rings 1200/1400 of about 40 mm to about 80 mm, and an inner passageway diameter of between about 20 mm to about 40 mm. In the figures, the rings are shown having generally the same diameter, but it will be understood that the diameter of the ring 1200 may selected to be greater than that of ring 1400, or the diameter of ring 1200 may be less than that of ring 1400. In one embodiment, a flexible tissue retractor having an inner passageway diameter smaller than that required to permit passage of a user's hand and generally less than about 50 mm can be desirable, so as to provide a access for multiple instruments but without requiring a relatively large incision.

The flexible tissue retractor 1000 may be formed to have a self supporting predefined shape, such as the shape shown in FIG. 1. By "self supporting" it is meant that when the refractor 1000 is placed on a substantially horizontal surface (e.g. flat table top), the retractor is able to maintain its shape without collapsing, with the passageway 1104 extending substantially vertically and with the portions 1120 and 1140 separated a predetermined distance from each other by portion 1160.

In FIGS. 1-3, the insert 2000 is shown pressed into or otherwise positioned within a passageway 1104 such that insert 2000 and the instrument openings 2014 are disposed below the ring 1200 and the annular portion 1120 of the flexible tissue retractor. As shown in FIG. 3, a member such as a retention feature in the form of an internal rib 1108 may be formed with or otherwise provide on the internal surface of the retractor. The rib 1108 can be positioned to prevent the insert 2000 from being pushed through the retractor 1000 and into the body cavity 40.

In FIGS. 2 and 3, the distal end of the insert 2000 and the instrument exits 2016 are shown extending generally at or below the distal ring 1400 and the distal portion 1160 of the flexible retractor. Accordingly, the insert 2000 is positioned within the retractor 1000 to provide a low profile, such that the instruments inserted into the openings 2014 and out of the exits 2016 can be pivoted with respect to the insert 2000 and/or each other at pivot points positioned distally of the upper, proximal ring 1200, such as at pivot points positioned within the incision. Such a low profile configuration allows seals associated with the instrument passageways in the insert 2000 to reside below ring 1200, and in particular, within the incision or within the abdominal cavity. Without being limited by theory, it is believed that positioning seals in the abdominal space may assist in preventing the seals from being collapsed or otherwise affected by tissue pressure, and may prevent tissue from closing instrument passageways or otherwise blocking or reducing visibility through the instrument passageways.

Figure 4:
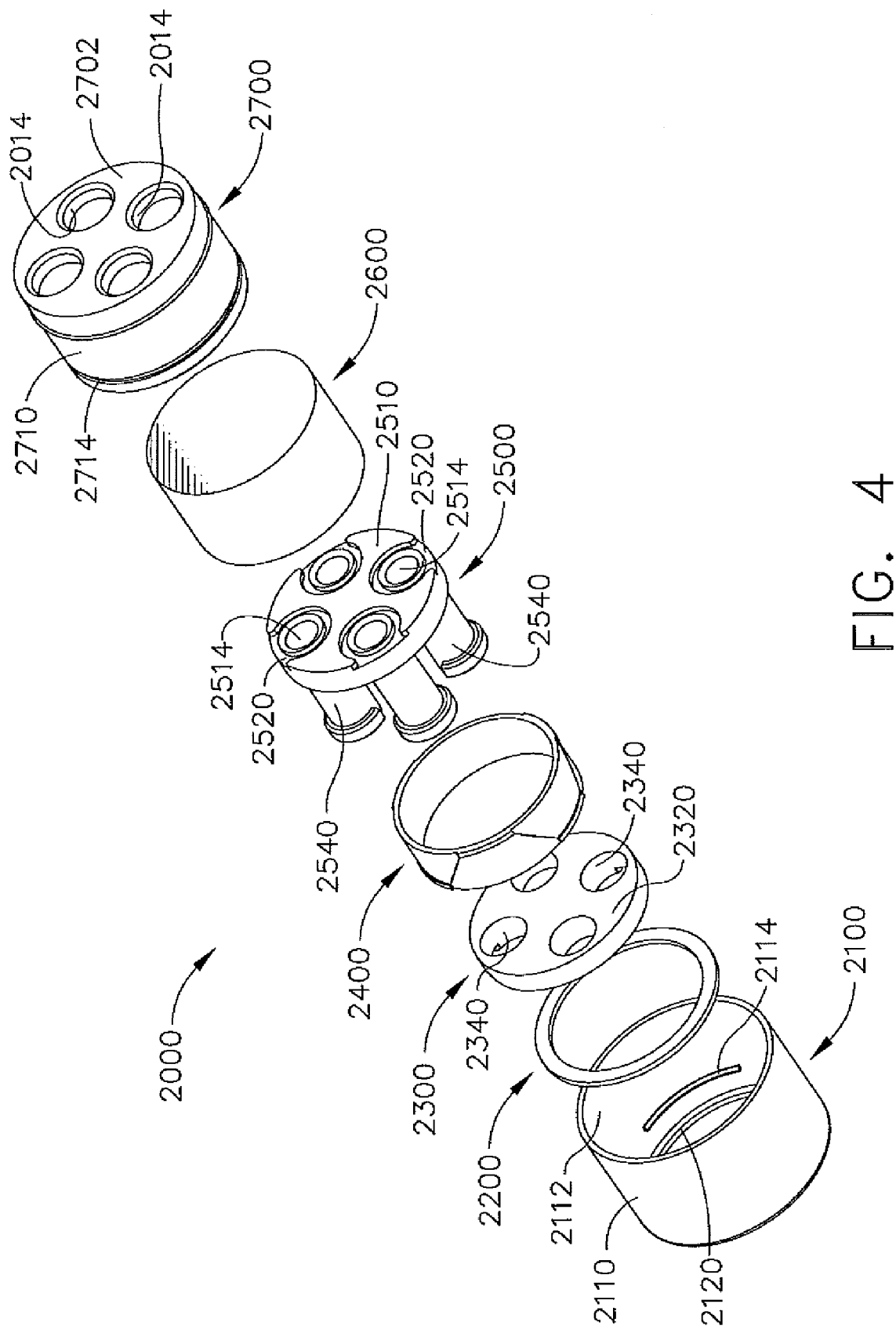
FIG. 4 is an exploded view of an insert of the type shown in FIG. 1.

Referring to FIGS. 3 and 4, the insert 2000 shown comprises an insert assembly. The insert assembly is shown comprising an outer body portion 2100, a bearing member 2200, an inversion constraint member 2300, a spacer 2400, an elastomeric instrument channel member 2500, a membrane seal 2600, and an inner housing 2700, as described more fully below.

Outer body portion 2100 is shown in the form of a generally cylindrical shell having a generally cylindrical outer surface 2110, an inner surface 2112, a distal ledge 2120 extending radially inwardly from surface 2112, and an internal surface feature, such as a circumferentially extending protrusions 2114.

The outer body portion 2100 may be a generally rigid, hard shell formed of a suitable material, such as polyethylene or other suitable medical grade materials, so that when the insert 2000 is inserted into the flexible retractor 1000, the outer body portion 2100 does not deform to any significant degree, but instead acts to stretch or otherwise expand the flexible retractor to maintain the passageway 1104 in a desired shape and size, or to provide the passageway with a predetermined size and shape.

The outer body portion 2100 shown may inserted into the retractor to deform the portion of the retractor spaced from and intermediate the rings 1200 and 1400. The outer body portion 2100 can be sized and shaped to pass through one or both rings 1200 and 1400 without deforming the rings. For instance, outer body portion 2100 may have a generally cylindrical outer surface having an outer diameter smaller than the inner diameter of ring 1200, and the outer surface can be sized to radially and circumferentially stretch the portion of the retractor associated with passageway 1104. Accordingly, the insert 2000 may provide the passageway 1104 extending through the incision with a generally circular cross-section of predetermined diameter. The advantages of ease of insertion of a flexible retractor are retained, while preventing the passageway 1104 from being narrowed or constricted by the incision. In addition, an insert having a generally cylindrical configuration provides a generally circular opening through the retractor, with a circle providing the maximum area per unit of perimeter length. A generally circular cross-section of the insert also allows for ease in providing for rotation of a portion of the insert, such as with respect to the outer surface of the insert and/or the refractor.

In one embodiment, the outer diameter of the body portion 2100 may be sized to be slightly larger than the inner diameter of passageway 1104 when retractor is free standing, without the insert 2000 disposed in the passageway 1104. After the refractor 1000 has been inserted into an incision, the insert 2000 may be inserted into refractor 1000. The insert 2000 may be sized to stretch the retractor, to at least slightly enlarge the passageway 1104, and the insert 2000 can frictionally engage the internal surface of passageway 1104. The insert 2000 can act to hold open the passageway 1104 against the compressive forces of the incision acting on the retractor 1000.

The outer body portion 2100 is shown having a generally cylindrical outer surface, but it will be understood that other outer surface shapes may be employed, including generally smooth or faceted outer surfaces. Suitable surface include, but are not necessarily limited to oval, elliptical, ovoid, oblong, and combinations thereof. For instance, it may be desirable to provide various inserts having different outer surface shapes and sizes to provide or assist in providing a passageway 1104 having a certain size and shape, depending on for instance the procedure being performed and/or the size of the incision. The size and shape of the outer surface of body portion 2100 may serve to deform the flexible member to provide at least a portion of the passageway with a predetermined size and shape. Additionally, the size and shape of the outer body portion may serve to provide frictional engagement of the outer body portion 2100 with the inner surface of the passageway 1104 in the flexible retractor.

Still referring to FIGS. 3 and 4, the inner housing 2700 includes an outer proximally facing top surface 2702 through which instrument openings 2014 may extend. The inner housing 2700 shown also has a generally cylindrical outer side surface 2710 extending distally from the top surface 2702. The instrument channel member 2500 is shown supported within inner body portion 2700. The instrument channel member 2500 defines a plurality of instrument channels 2550, each channel 2550 generally aligned with and extending from a proximal opening 2014 to a distal exit 2016. The membrane seal 2600 is shown captured between the inner housing 2700 and a proximal end of the instrument channel member 2500. The membrane seal 2600 provides a seal for preventing loss of insufflation through an instrument opening 2014 prior to insertion of an instrument through the opening. The membrane seal 2600 may be in the form of a thin membrane formed of a flexible material which can be punctured or otherwise pierced by a surgical instrument. In one embodiment, the seal 2600 comprises a membrane formed of polyurethane having thickness of less than about 0.010 inch, and in particular the membrane can have a thickness of about 0.006 inch. Alternatively, zero closure seals such as a duck bill seal or other suitable seals for sealing in the absence of instrument may be employed in association with the openings 2014.

The distal ledge 2120 of the outer body portion 2100 provides an axial thrust support surface on which bearing member 2200 may be rotatably supported (see for instance FIG. 3). Bearing member 2200 may serve to provide rotational support for an assembly comprising the inner body portion 2700 and instrument channel member 2500, such that the assembly is able to rotate relative to the outer body portion 2100 about an axis 70 extending generally longitudinally through the passageway 1104 in the retractor 1000 (see FIG. 3). Bearing member 2200 may be formed of any suitable material, such as high density polyethylene.

Accordingly, bearing member 2200 may be provided so that when the insert 2000 is pressed into place within flexible retractor 1000, the outer body portion 2100 may remain generally stationary with respect to the retractor 1000, while the instrument channel member 2500 is rotatable within the retractor. Rotation of the member 2500 permits rotational positioning of the instrument openings 2014 and passageways 2550 to provide desired positioning of one or more instruments extending through insert 2000.

The instrument channel member 2500 is shown comprising a plurality of instrument channels 2540, each instrument channel comprising an instrument passageway 2550. The instrument channel member 2500 may be advantageously formed as a one piece, unitary structure formed from a deformable, resilient material such as polyisoprene, Kraton, or Sanoprene, so that each instrument channel 2540 is independently deformable with respect to the housing 2700 and to the other instrument channels. Accordingly, instruments inserted into the instrument passageways 2550 may be angled and/or pivoted with respect to each other, allowing for increased freedom of motion of each instrument relative to the others. If desired, a seal member 2544 or other constriction may be provided at the distal end of each instrument channel 2540 for providing sealing about an instrument positioned within the instrument channel 2540.

In the figures, the instrument channels 2540 are shown to be generally cylindrical in shape, and extending distally from a proximal base 2510. Openings 2514 in the base 2510 correspond to and are generally aligned with the instrument openings 2014 by recesses 2520 formed in the upper surface of the base 2510. The recesses 2520 may be positioned to mate with features on the underside (distal side) of the inner housing 2700.

The protrusions 2114 formed in the inner surface of outer body portion 2100 may operatively engage a feature, such as a circumferentially extending groove 2714 formed in an outer cylindrical surface 2710 of the inner housing 2700. The protrusions 2114 engage groove 2714 to restrain the inner housing 2700 axially (i.e. in the proximal and distal directions) with respect to the outer body portion 2100, while permitting rotation of the inner body portion 2700 with respect to the outer body portion 2100. Alternatively, the body portion 2100 could include a groove, and the inner housing 2700 could include a protrusion for engaging such a groove.

Inversion constraint member 2300 may be provided to prevent instrument channels 2540 from becoming "inverted" (e.g. in the manner of a shirt sleeve being pulled inside out) when an instrument is withdrawn from the channel 2540. The member 2300 is shown having a generally disc shaped body 2320 having apertures 2340 extending therethrough. Each aperture 2340 can be sized to fit over the distal end of a corresponding instrument channel 2540. The member 2300 may be formed of any suitable material, including for instance polyisoprene, Sanoprene, or Kraton. The flexibility of the member 2300 may be tailored with respect to the flexibility of more proximal portions of the insert 2000. For instance, if member 2300 is made relatively more flexible than a proximal portion of the insert 2000 (such as for instance the top surface of the housing 2700), then instruments inserted in the instrument channels will tend to pivot about a fulcrum associated with the more proximal portion of the insert. Alternatively, if the member 2300 is made relatively more rigid with respect to the more proximal portions of the insert 2000, then the instruments will tend to pivot about a fulcrum associated with the member 2300. As shown in FIG. 3, the member 2300 may be positioned axially between bearing member 2200 and spacer 2400, and the member 2300 may be positioned radially inward of the distal portion of the inner housing 2700.

Figure 5:
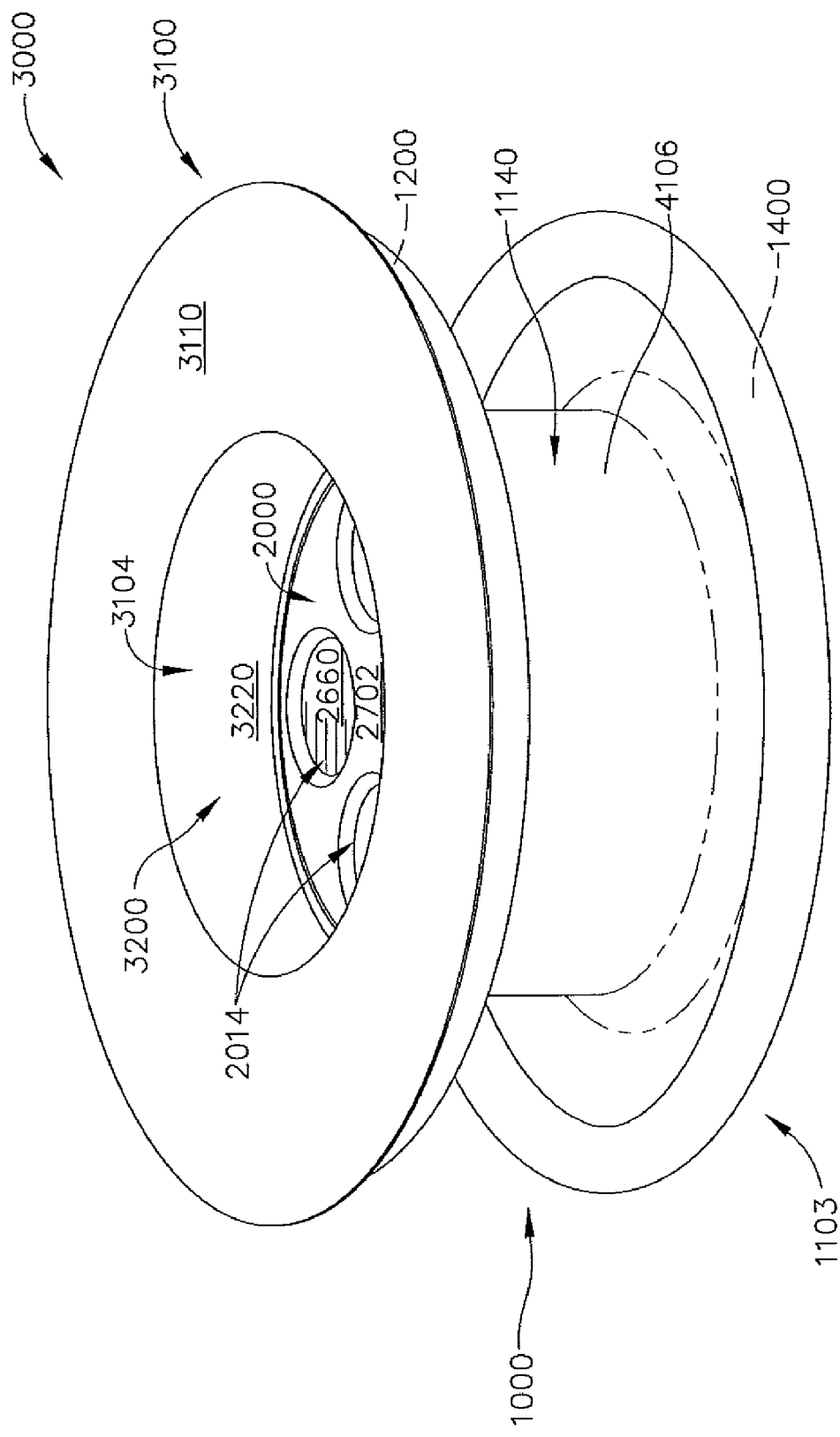
FIG. 5 is a perspective, proximal view showing an alternative access device comprising an assembly of an insert, a flexible tissue retractor, and a sleeve, the sleeve shown as including a generally annular portion disposed over the proximal end of the flexible tissue retractor, and the sleeve shown as including a generally cylindrical portion extending distally from the annular portion, at least a portion of the generally cylindrical portion of the sleeve disposed between the insert and the flexible tissue retractor.
Figure 6:
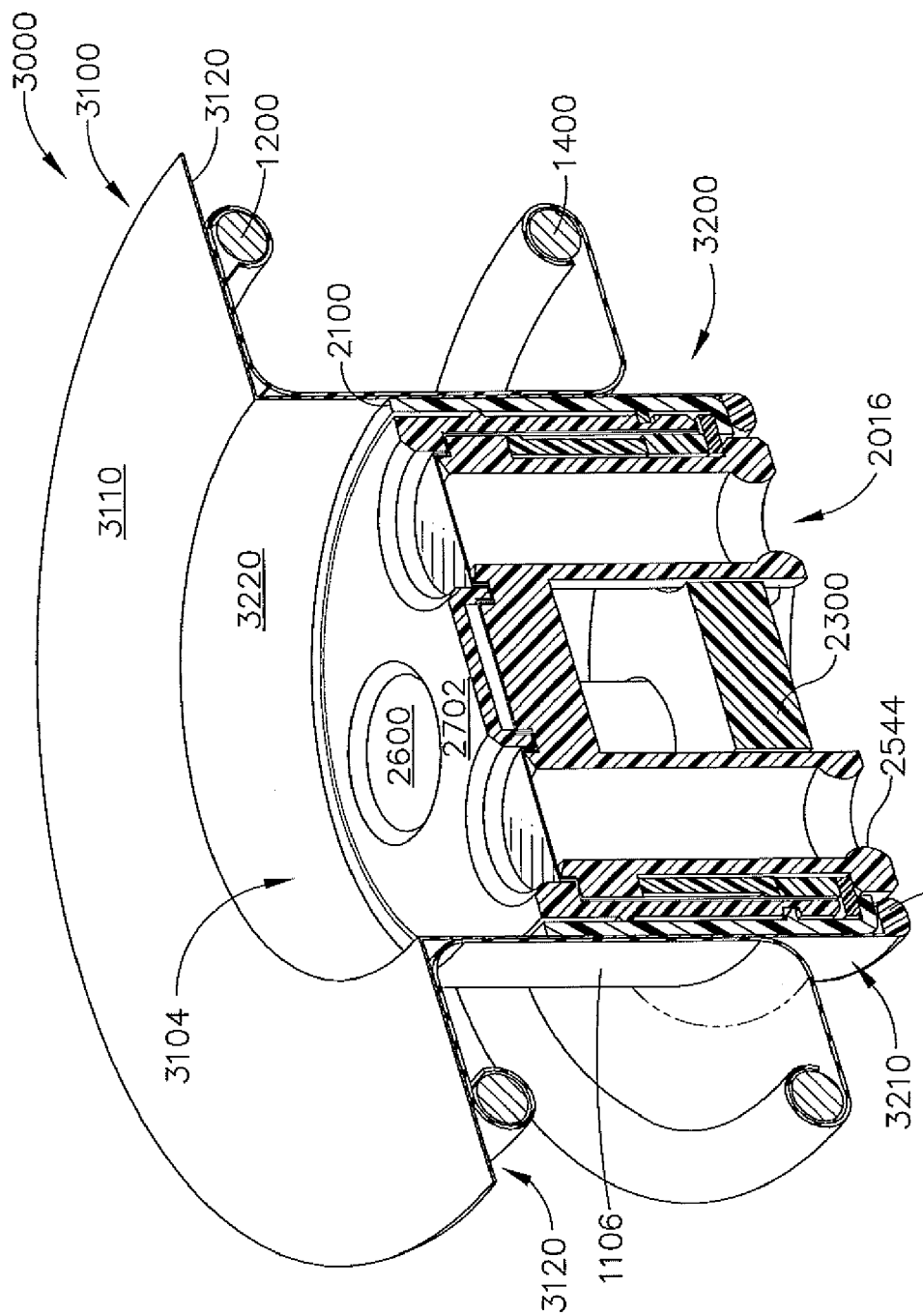
FIG. 6 is a cross-sectional view of the device of the type shown in FIG. 5, and showing the generally cylindrical portion extending distally beyond the distal end of the tissue retractor and the insert, the distal end of the cylindrical portion shown having a member in the form of a generally circumferentially extending rib or ledge for preventing the insert from being pressed into the body cavity and to assist in withdrawing the insert from the tissue retractor.

FIGS. 5 and 6 and illustrate an alternative embodiment of an access device according to the present invention. The access device shown comprises an assembly of a flexible tissue retractor 1000, an insert 2000, and a sleeve 3000. The flexible tissue retractor 1000 and the insert 2000 can be of any suitable form, including as described above with respect to FIG. 1-4.

Sleeve 3000 may be provided to assist in preventing the insert 2000 from being pressed through the retractor 1000 and into a body cavity, and to assist in removing the insert 2000 from the retractor 1000. For instance, during a surgical procedure it may be desirable to interchange one or more inserts in a tissue retractor 1000 without removing the tissue retractor 1000 from the incision. Sleeve 3000 may also be provided to protect the retractor 1000 from being torn or otherwise damaged by instruments inserted through insert 2000. In one embodiment, multiple inserts 2000 may be provided for a specific procedure, each insert having a different shape, a different size, a different number of instrument openings, and/or different instrument opening sizes. Or, it may be desirable to remove an insert 2000 from the retractor positioned in the incision, such as to withdraw an instrument, apparatus, tissue, or body organ through the passageway of the tissue retractor 1000.

Referring to FIGS. 5 and 6, the sleeve 3000 may comprise a generally annular portion 3100 and a generally cylindrical portion 3200. The generally annular portion 3100 is shown having a generally flat proximal (upper) surface 3110, and an opposite, generally flat distal (downward) surface 3120. Sleeve distal surface 3120 may abut or otherwise contact or face the proximal portion of flexible tissue refractor 1000 when the sleeve 3000 is fully positioned with respect to retractor 3000 and insert 1000.

The generally cylindrical portion 3200 is shown extending distally from, and at substantially a right angle to, the annular portion 3100. The generally cylindrical portion 3200 is shown including a radially outwardly facing surface 3210 and an inwardly facing surface 3220. The inwardly facing surface 3220 provides a passageway 3104. The generally cylindrical portion 3200 extends at least partially through the flexible tissue retractor 1000, and in FIGS. 5 and 6 the generally cylindrical portion 3200 extends through the retractor 1000 to extend distally beyond the distal end of the retractor 1000.

In FIGS. 5 and 6, the insert 2000 is shown diposed within the passageway 3104 provided by generally cylindrical portion 3200 of sleeve 3000. Sleeve portion 3200 is, in turn, shown disposed within the flexible tissue retractor 1000. The insert 2000, sleeve 3000, and flexible tissue retractor may be assembled in any desired order, either before or after the tissue retractor is positioned in an incision. For instance, insert 2000 may be pressed into sleeve 3000, and the sleeve/insert subassembly may then be pressed into retractor 1000 either before or after the retractor is positioned in the incision. Alternatively, the sleeve 3000 may be pressed or otherwise inserted into the retractor either before or after the retractor is positioned in the incision, and the insert may then be pressed into the sleeve.

Generally, the tissue retractor 1000 will first be inserted into an incision, such as by deforming one or both rings 1200/1400 to insert the retractor in the incision, or by using an insertion tool to insert the retractor in the incision. The sleeve 3000 may then be inserted into the retractor 1000, such as by pressing the sleeve into the retractor. The insert 2000 may then be inserted into the sleeve 3000.

The sleeve 3000 is shown having a member such as a retention feature for preventing the insert from being pressed completely through the sleeve/retractor into the body cavity, and to assist in removing the insert 2000 from the retractor. Referring to FIG. 6, a retention feature in the form of a generally circumferentially extending ledge or lip 3300 is shown extending generally radially inwardly at a distal end of the generally cylindrical portion 3200 of sleeve 3000. The lip 3300 may be circumferentially continuous, and may be sized and shaped to abuttingly engage a portion of the insert, such as the distal end of the outer body portion 2100.

In the embodiment shown in FIGS. 5 and 6, when the insert 2000 and the sleeve 3000 are fully inserted within retractor 1000, the seals 2544 are positioned below the distal end of the retractor 1000. Such an arrangement can provide an instrument pivot point below the retractor, and within the body cavity.

If desired, the insert 2000 and/or sleeve 3000 may be partially withdrawn from the fully inserted configuration shown in FIGS. 5 and 6, in a proximal direction to reposition the distal end of the insert 2000 with respect to the retractor 1000. Accordingly, the positions where the surgical instruments exit the insert 2000 can be varied in a generally continuous manner along the axis 70, and the point where instruments exit the insert 2000 can be located at a plurality of positions within the passageway provided by the refractor, or distally below the distal end of the retractor.

If desired, a kit may be provided with different inserts 2000, different tissue retractors 1000, and/or different sleeves 3000. For instance, the kit may include a plurality of tissue retractors 1000, each sized and/or shaped for a different incision size. The kit may include a plurality of inserts 2000 having different instrument openings sizes and/or configurations. The kit may include sleeves with generally cylindrical portions having different lengths and/or diameters.

In order to withdraw the insert 2000 from the refractor 1000 and incision, a portion of the sleeve 3000, such as the annular portion 3100, may be gripped with one or both hands (such as at opposite sides of the annular portion 3100), and the sleeve may be pulled proximally (upward in FIGS. 5 and 6) to withdrawn the sleeve 3000 and insert 2000 from the tissue retractor 1000.

The sleeve 3000 may be formed of a non-metallic plastic or elastomeric material. The sleeve 3000 may have a thickness of between about 0.004 inch and 0.025 inch, and may be formed of a relatively low friction, high puncture resistant material having a relatively high elongation before tearing, and be relatively resistant to silicone or other lubricants without breaking down or degrading. One suitable sleeve 3000 can be formed of sheet or film having a thickness of about 0.005 inch to about 0.007 inch. Sleeve 3000 may be formed to have a coefficient of friction less than that of the retractor 1000, and the coefficient of friction of the sleeve 3000 can be less than about 0.25, more particularly, less than about 0.20, and still more particularly, less than about 0.15.

In one embodiment, sleeve 3000 may be formed of a relatively stiff, non-metallic plastic or elastomeric material having a hardness greater than the hardness of the tissue retractor, and a flexibility less than that of the tissue retractor. In another embodiment, the sleeve may be formed of a material that is relatively soft and flexible. One suitable material from which sleeve 3000 may be formed is a thermoplastic polyurethane elastomer such as a Pellethane brand polyurethane available from Dow Chemical.

Multiple inserts 2000 may be provided, such as two, three, or more inserts may be provided in a kit form for use in a single surgical procedures. For example, a first insert may be provided having two or more instrument openings, and a second insert may also be provided having multiple instrument openings. The first and second inserts may have the same number of instrument openings, or a different number of instrument openings.

Figure 7:
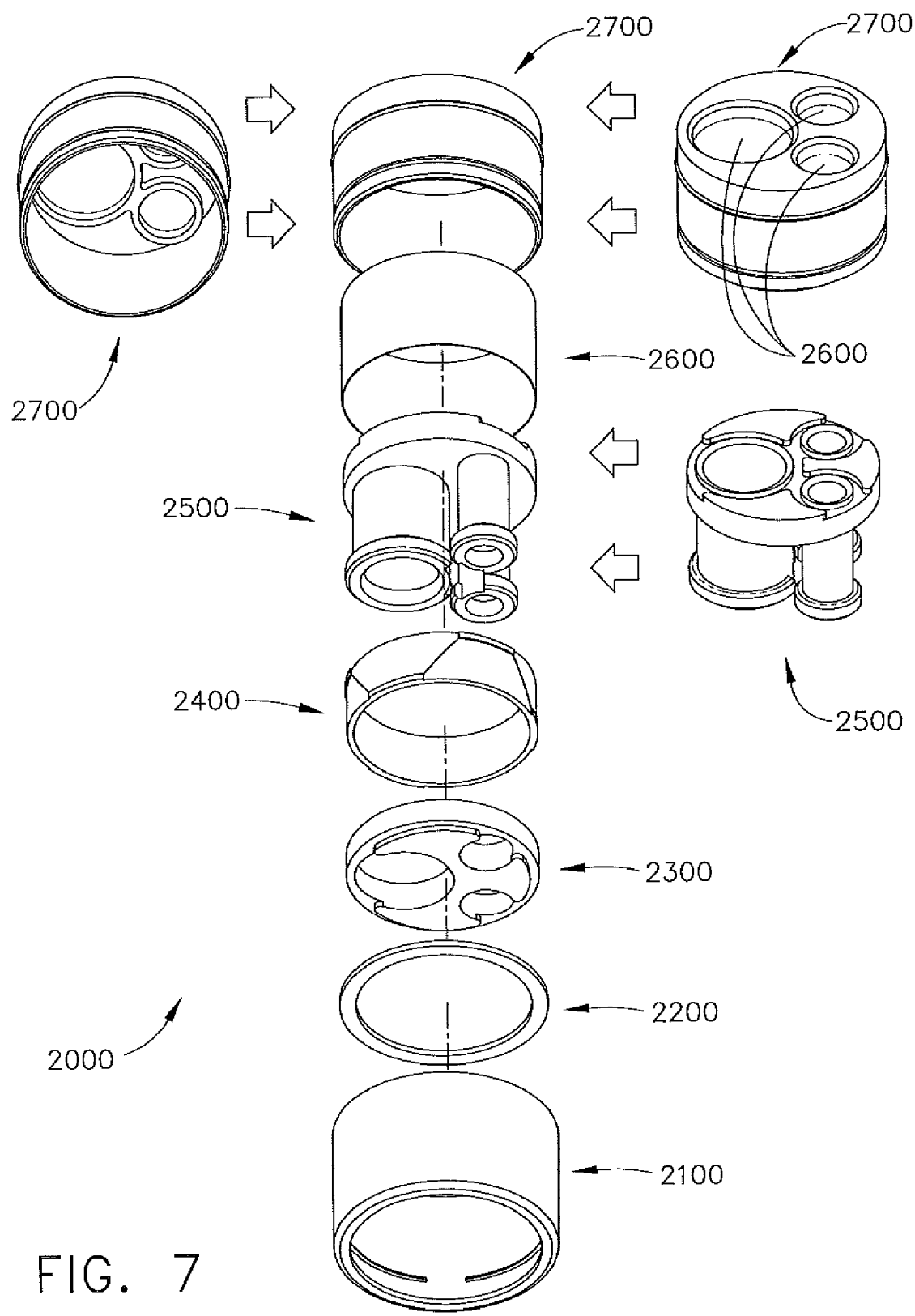
FIG. 7 is an schematic exploded view of an insert similar to that shown in FIG. 4, but having three versus four instrument openings, including one relatively larger instrument opening (such as to receive a laparascope or other relatively larger diameter device), and two relatively smaller instrument openings (such as to receive relatively smaller devices, such as 5 mm graspers, clip appliers, or the like).

FIG. 7 is an schematic exploded view of an insert 2000 similar to that shown in FIG. 4, but having three instrument openings 2600, versus four instrument openings as shown in FIG. 1. In FIG. 7, the three instrument openings include one relatively larger instrument opening (such as to receive a laparascope or other relatively larger diameter device), and two relatively smaller instrument openings (such as to receive relatively smaller devices, such as 5 mm graspers, clip appliers, or the like). As shown in FIG. 7, the instrument channel member 2500 has three instrument channels corresponding to the three instrument openings, with one of the instrument channels shown being relatively larger in diameter than the other two instrument channels. The insert 2000 of FIG. 7 can have generally the same shape and diameter as that of FIG. 1. Alternatively, if desired, the insert could have a different diameter and/or a different shape.

Figure 8:
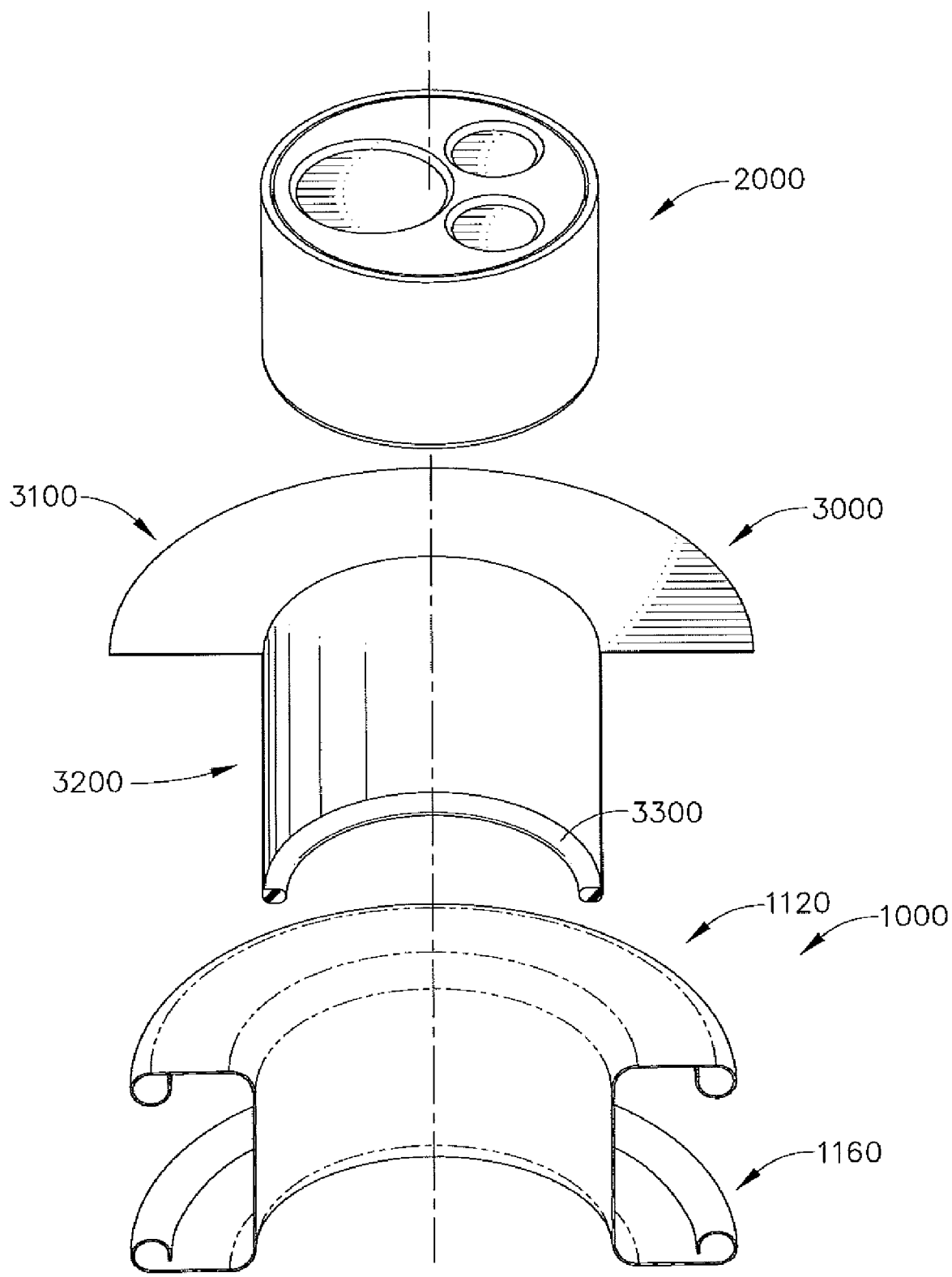
FIG. 8 is a schematic depiction of how the insert of FIG. 7 can be inserted into a sleeve (shown in half section), and the insert and sleeve can, in turn, be inserted into a flexible tissue retractor (also shown in half section).

FIG. 8 is a schematic depiction of how the insert of FIG. 7 can be inserted into a sleeve 3000 (shown in half section), and the insert 2000 and sleeve 3000 can, in turn, be inserted into a flexible tissue retractor 1000 (also shown in half section). As described above, the sleeve 3000 can include a retention feature in the form of a generally circumferentially extending ledge or lip 3300 is shown extending generally radially inwardly at a distal end of the generally cylindrical portion 3200 of sleeve 3000. The lip 3300 may be circumferentially continuous, and may be sized and shaped to abuttingly engage a portion of the insert, such as the distal end of the outer body portion 2100 of the insert. If desired, the sleeve 3000 can be formed of a relatively resilient material, and the inner diameter of the portion 3200 of the sleeve 3000 can be sized to engage the outer surface of the insert (such as by having a slightly smaller diameter than the insert 2000) so that the insert can be releasably positioned at multiple insertion depths within the portion 3200. In this way the insert 2000 can be positioned at multiple insertion depths with respect to the flexible tissue retractor, with feature 3300 being operable to prevent the insert from being inadvertently pushed into the body cavity.

Figure 9:
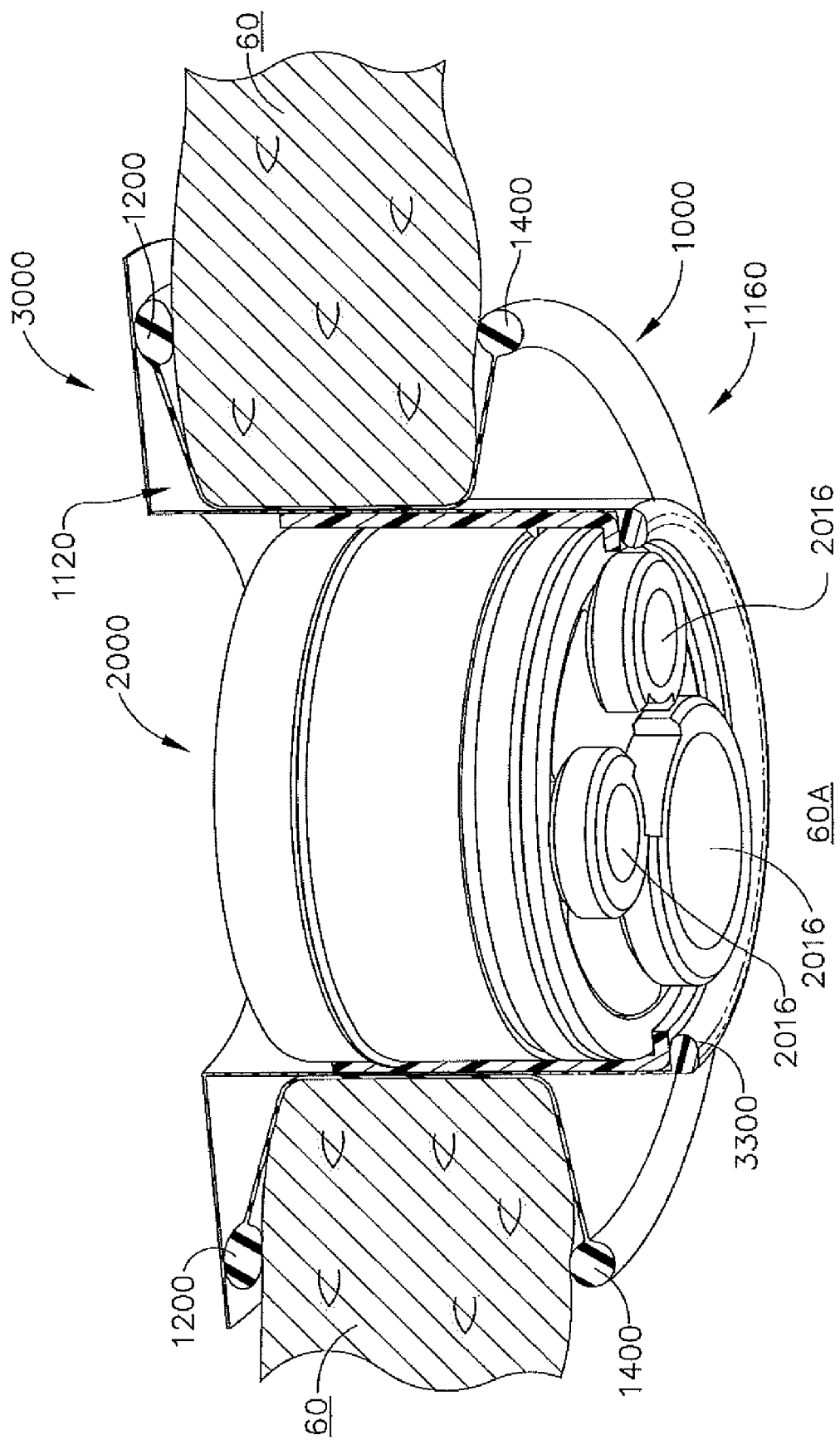
FIG. 9 illustrate the insert, sleeve, and tissue retractor positioned in tissue, with the insert shown inserted into and supported by the sleeve, and the sleeve, in turn, supported in the tissue retractor, with the sleeve and retractor shown in half section, and FIG. 9 illustrating the sleeve having a length longer than the axial length of the retractor, such that the sleeve can be positioned at various depths within the retractor, and such that in FIG. 9 the distal portion of the insert is shown positioned below the abdominal wall, and the distal portion of the insert abutting a retention feature in the form of an internal lip at the distal end of the sleeve, the retention feature preventing the insert from being pushed through the sleeve and into the abdominal cavity, and the lip facilitating removal of the insert with the sleeve when the sleeve is withdrawn from the flexible retractor.

FIG. 9 illustrates a tissue retractor 1000 disposed in an incision in tissue 60, with insert 2000 releasably supported in the sleeve 3000, and sleeve 3000 in turn releasably supported within the tissue retractor 1000. The insert 2000 is shown disposed at the distal end of sleeve 3000, with the distal end of the insert abutting against member/retention lip 3300 of the sleeve.

FIG. 9 also illustrates the sleeve 3000 can have an axial length longer than the axial length of the retractor 1000. If desired, the sleeve can be positioned at various depths within the retractor, so that the distal end of the sleeve (e.g. the distal end of the cylindrical portion 3200) can be positioned proximal or distal of the distal end of the retractor. In FIG. 9, the distal end of the sleeve is shown disposed distally (below) the distal end of the tissue retractor 1000, so that the instrument exits 2016 of the insert 2000 are positioned below the abdominal wall. The retention feature (e.g. lip member 3300) prevents the insert from being unintentionally pushed into the abdominal cavity 60A. The feature 3300 also facilitates removal of the insert 2000 with the sleeve 3000 when the sleeve is withdrawn proximally from the flexible retractor 1000. Accordingly, the retractor can be left in the incision after removal of the sleeve 3000 carrying the insert.

Figure 10:
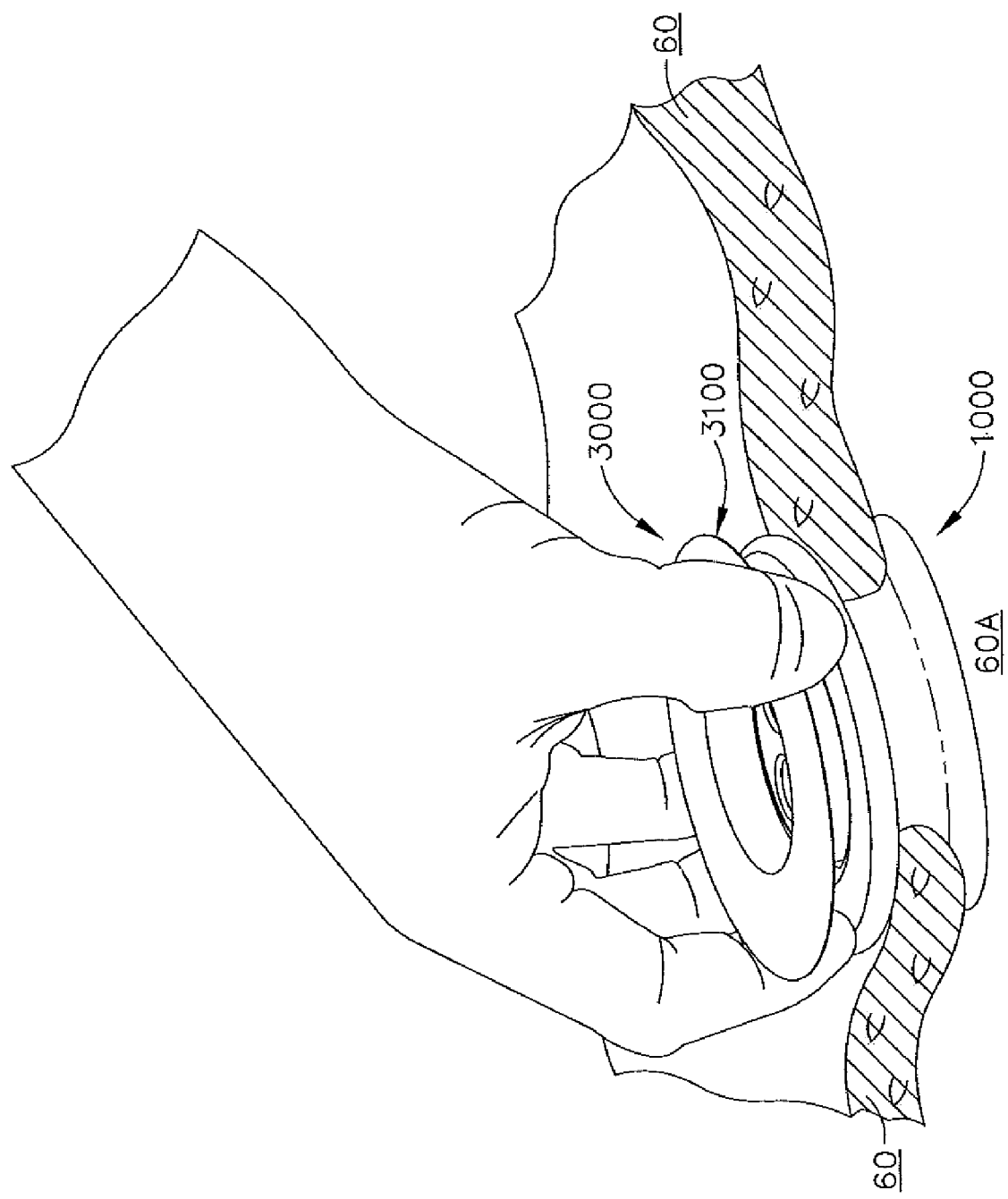
FIG. 10 is a perspective view illustrating how the sleeve and insert can be removed by fingers of a single hand grasping the edges of the sleeve and lifting the sleeve proximally (upward in FIG. 10), with the insert retained by the sleeve and the insert being removed along with the sleeve when the sleeve is withdrawn from the retractor, and with the retractor left in place in the incision.

FIG. 10 is a perspective view illustrating how the sleeve 3000 and insert 2000 can be removed by fingers of a single hand grasping the edges of the portion 3100 of sleeve 3000 and lifting the sleeve proximally (upward in FIG. 10), with the insert carried and retained by the sleeve 3000. The insert is shown being removed along with the sleeve when the sleeve is withdrawn from the retractor 1000, and with the retractor left in place in the incision in tissue 60.

Figure 11:
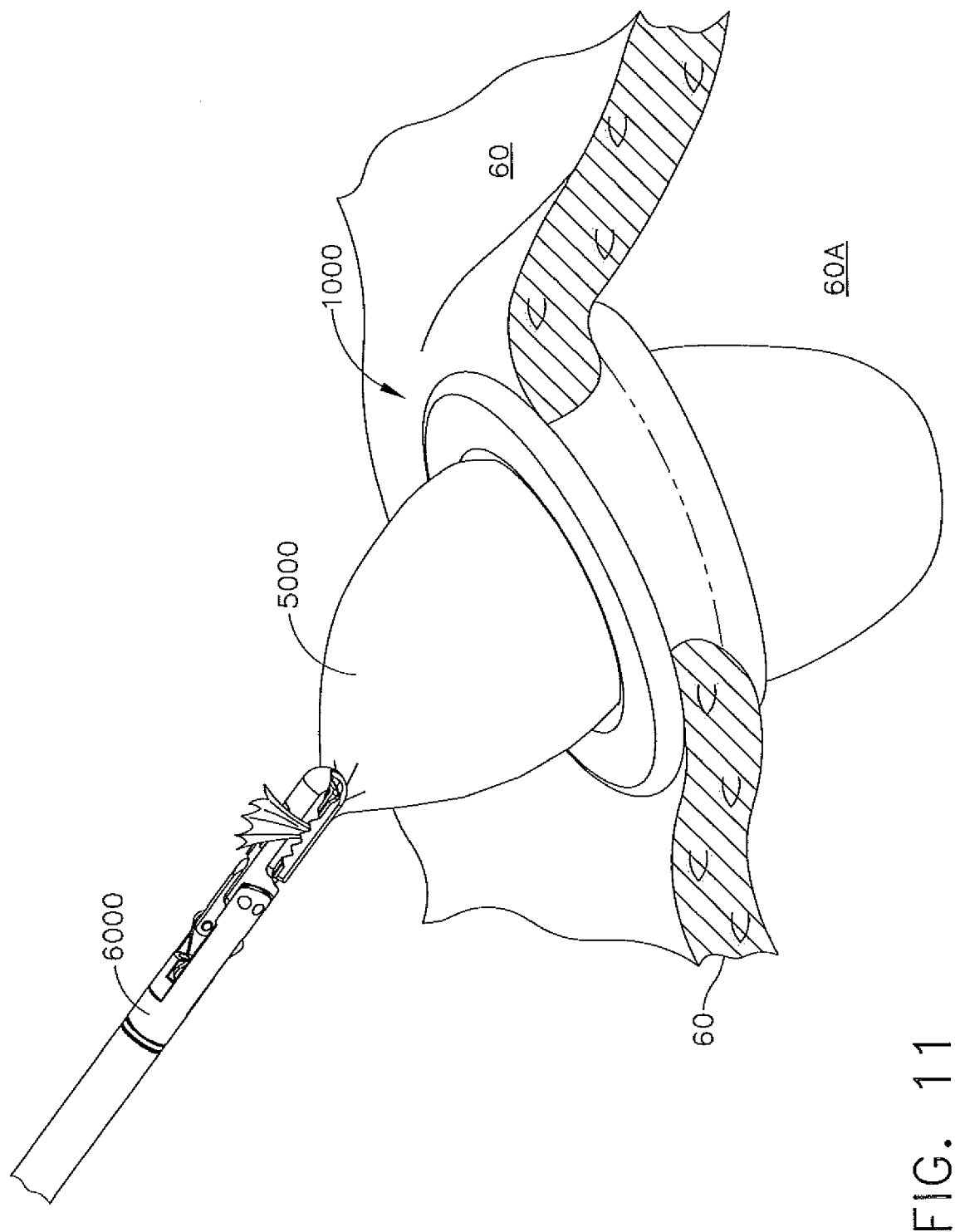
FIG. 11 is a perspective view showing how, once the sleeve and insert have been removed from the flexible retractor, a specimen and/or specimen bag can be removed from the body through the flexible retractor.

FIG. 11 is a perspective view showing how, once the sleeve 3000 and insert 2000 have been removed from the passageway provided by flexible retractor 1000, a specimen and/or specimen bag 5000 can be removed proximally (upward in FIG. 11) from the body cavity (e.g. abdominal cavity 60A) through the passageway of the flexible retractor 1000, such as with an grasper instrument 6000 inserted through the passageway of the retractor.

Figure 12:
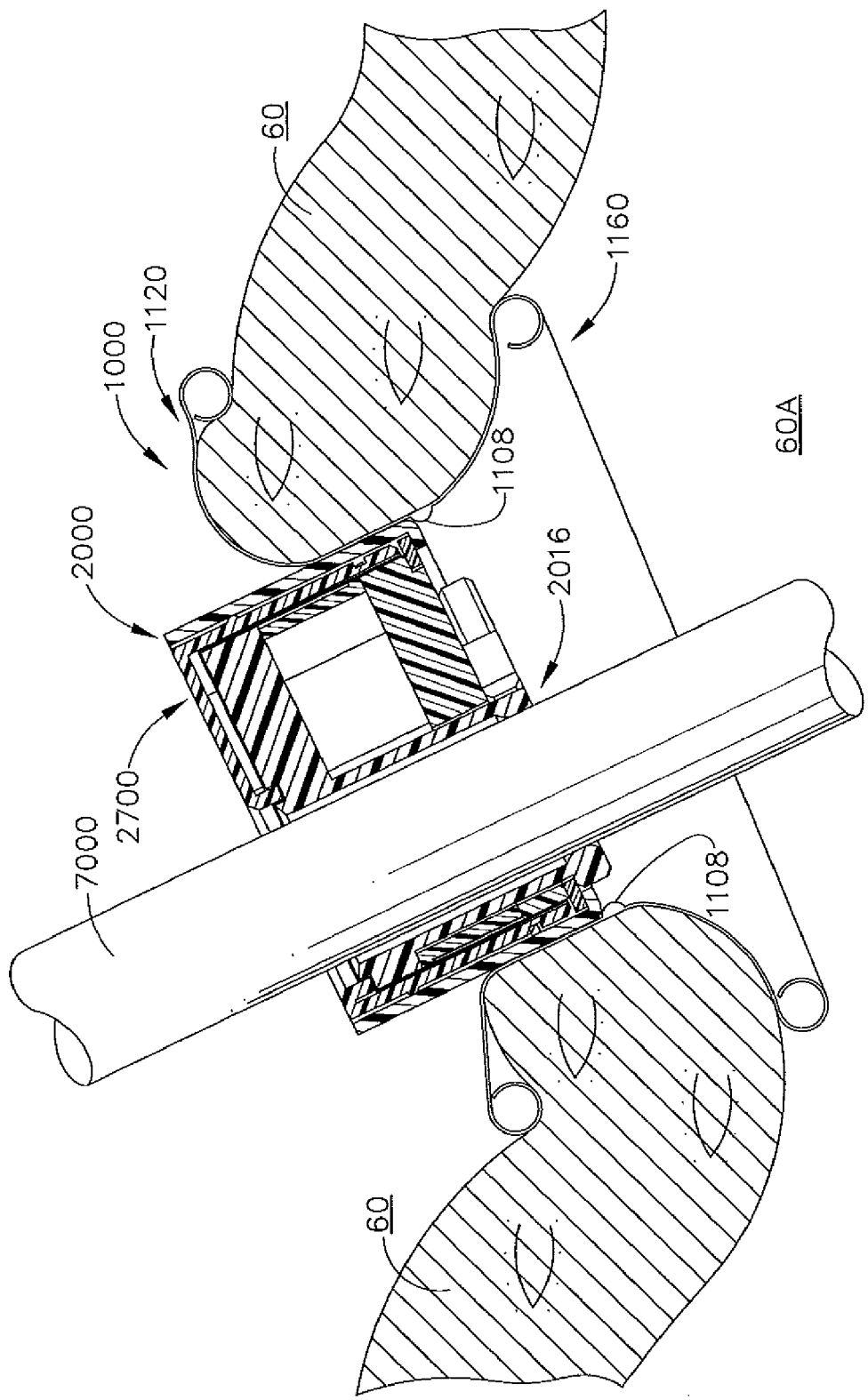
FIG. 12 is a cross-sectional schematic illustration of an embodiment where an insert is disposed within a flexible retractor, where the flexible retractor has an internal retention feature in the form of an internal rib for retaining the insert at a desired depth within the retractor, and FIG. 12 illustrating how the insert's flexible support within the retractor allows an instrument extending through the insert to pivot the insert itself, such as to provide an improved range of motion of the instrument over seals mounted above or below the retractor.

FIG. 12 shows a cross-sectional schematic illustration of an embodiment where an insert 2000 is disposed within a flexible retractor 1000, without the use of a sleeve 3000. The flexible retractor 1000 is shown having an internal retention feature in the form of an internal rib or lip 1108 for retaining the insert 2000 at a desired depth within the retractor. In FIG. 12, the lip 1108 is shown positioned about midway along the length of the passageway provided by retractor 1000, so that the distal end of the insert 2000 is disposed about midway along the length of the passageway of the retractor.

FIG. 12 illustrates how the flexible support of the insert within the flexible retractor 1000 allows an instrument 7000 (e.g. a laparascope or instrument for manipulating/grasping tissue) extending through an instrument channel of the insert 2000 can be employed to pivot the insert 2000 itself, such as to provide an improved range of motion of the instrument, as compared to the range of motion provided by instrument supports and seals mounted above or below a retractor.

Figure 13:
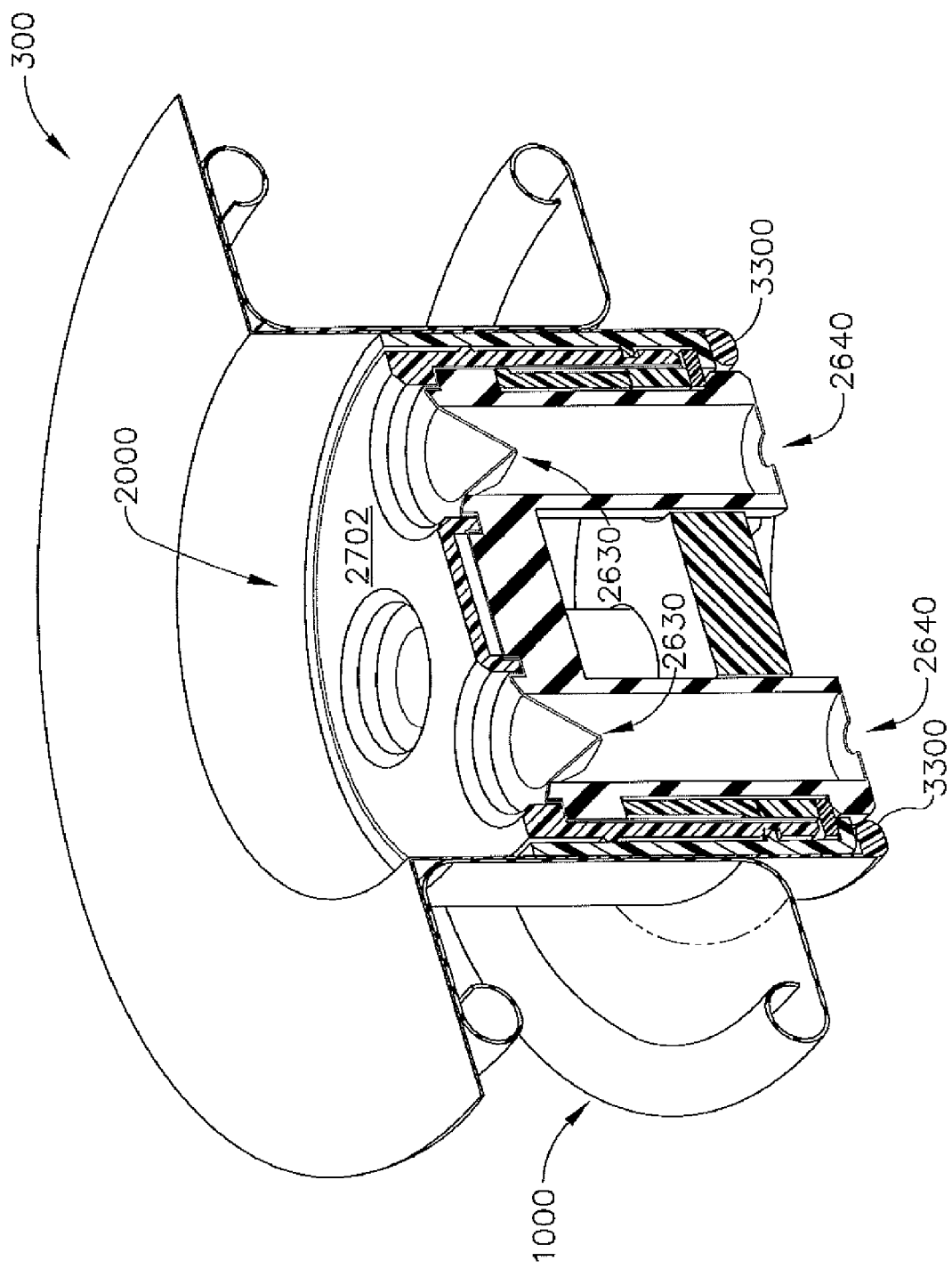
FIG. 13 provides a schematic cross-sectional illustration of an insert, sleeve, and retractor, where the insert includes zero closure seals in the form of duckbill seals at the proximal end of the insert for sealing instrument access channels when no instrument is inserted through the channel, and instrument seals in the form of septum seals for sealing about instruments inserted into the instrument channels.

FIG. 13 provides a schematic cross-sectional illustration of an assembly comprising an insert 2000, sleeve 3000, and retractor 1000, where the insert includes zero closure seals in the form of duckbill seals 2630 associated with the proximal end of the instrument access channels (for sealing instrument access channels when no instrument is inserted through the channel), and instrument seals in the form of septum seals 2640 operatively associated with the distal ends of the instrument access channels for sealing about instruments inserted into the instrument channels. Alternatively, the seals 2640 could be provided at the proximal end of the insert, and the seals 2630 could be provided at the distal end of the insert.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A medical device comprising:
a tissue retractor comprising a flexible member having an outer surface for engaging a body incision and an inner surface defining a passageway; and
an insert releasably supported within the passageway defined by the flexible member, wherein the insert comprises at least one instrument opening, the insert comprising an insert assembly having an outer portion and an inner portion wherein the inner portion is rotatable with respect to the outer portion.

2. The medical device of claim 1 wherein the insert comprises an outer surface sized and shaped to deform the flexible member to provide at least a portion of the passageway with a predetermined size and shape.

3. The medical device of claim 1 wherein the insert comprises a generally cylindrical outer surface sized to radially stretch the flexible member to have a generally circular cross-section of predetermined diameter upon insertion of the insert within the passageway.

4. The medical device of claim 1 wherein the flexible member has a proximal end and a second distal end, and wherein the insert is releasably supported within the passageway at a position spaced distally from the proximal end of the flexible member.

5. The medical device of claim 1 wherein the insert comprises a plurality of instrument openings.

6. The medical device of claim 1 wherein a portion of the insert is rotatable with respect to the flexible tissue retractor.

7. The medical device of claim 1 wherein the outer portion of the insert assembly engages the inner surface of the flexible member of the tissue retractor.

8. The medical device of claim 1 wherein the outer portion of the insert assembly frictionally engages an inner surface of the flexible member.

9. The medical device of claim 1 wherein the outer portion comprises a generally cylindrical sleeve.

10. The medical device of claim 1 wherein the outer portion comprises a ledge for restricting axial movement of the inner portion into a body cavity.

11. The medical device of claim 1 wherein the insert assembly comprises a rotation bearing positioned to support the inner portion axially while permitting rotation of the inner portion relative to the outer portion.

12. A medical device comprising:
a flexible tissue retractor having an outer surface for engaging a body incision and an inner surface for defining a body access passageway; and
an insert adapted to be inserted within the flexible tissue retractor, the insert comprising:
an outer sleeve sized and shaped to engage and deform a portion of the inner surface of the flexible tissue retractor;
a housing disposed at least partially within the outer sleeve, the housing having an upper surface comprising a plurality of instrument openings, the housing being rotatable with respect to the outer sleeve; and
at least one seal associated with each instrument opening.

13. The medical device of claim 12 wherein the insert further comprises an instrument channel member comprising a plurality of tubular instrument channels, each tubular instrument channel substantially aligned with an instrument opening in the housing.

14. The medical device of claim 13 wherein the housing and instrument channel member are rotatably supported with respect to the outer sleeve.

15. The medical device of claim 13 wherein the instrument channel member comprises a unitary, flexible structure, and wherein each tubular instrument channel is independently deformable with respect to the housing and the other tubular instrument channels.

16. The medical device of claim 13 further comprising an inversion restriction member having a plurality of openings there through, and wherein a tubular instrument channel extends axially through each opening of the inversion restriction member.

17. A medical device comprising:
a flexible tissue retractor having a first end, a second end, and a flexible member extending intermediate the first and second ends; and
an insert comprising (i) an outer portion and (ii) an inner portion having a plurality of instrument openings, wherein the inner portion is rotatable with respect to the outer portion, the insert adapted to be releasably inserted within the flexible member intermediate the first and second ends of the retractor.

18. The medical device of claim 17, wherein the flexible tissue retractor comprises a first deformable ring associated with the first end of the tissue retractor and a second deformable ring associated with the second end of the tissue retractor.

19. The medical device of claim 18 wherein the insert is sized and shaped to deform a portion of the flexible member intermediate the first and second deformable rings.

20. The medical device of claim 18 wherein the insert is sized to pass through the first deformable ring without deforming the first deformable ring.

* * * * *